United States Patent [19]
Lepley, Jr. et al.

[11] 4,168,708
[45] Sep. 25, 1979

[54] BLOOD VESSEL OCCLUSION MEANS SUITABLE FOR USE IN ANASTOMOSIS

[75] Inventors: Derward Lepley, Jr., Elm Grove; Donald C. Mullen, River Hills, both of Wis.

[73] Assignee: Medical Engineering Corp., Racine, Wis.

[21] Appl. No.: 789,208

[22] Filed: Apr. 20, 1977

[51] Int. Cl.$^2$ .............................................. A61B 17/00
[52] U.S. Cl. .................................... 128/325; 128/1 R
[58] Field of Search ............... 128/325, 341, 344, 343, 128/348, 1 R, 350 R; 138/94, 91, 89

[56] References Cited
U.S. PATENT DOCUMENTS

| | | | |
|---|---|---|---|
| 3,095,877 | 7/1963 | Rowan | 128/325 X |
| 3,392,922 | 7/1968 | Jorgensen | 128/350 R X |
| 3,768,102 | 10/1973 | Kwan-Gett et al. | 128/1 R X |
| 3,815,578 | 6/1974 | Bucalo | 128/1 R |
| 3,834,394 | 9/1974 | Hunter et al. | 128/325 |
| 3,889,685 | 6/1975 | Miller et al. | 128/344 X |

Primary Examiner—Robert W. Michell
Assistant Examiner—Michael H. Thaler
Attorney, Agent, or Firm—Quarles & Brady

[57] ABSTRACT

A T-shaped blood vessel occluder has a stem with a pair of opposing arms at one end forming a bar. Generally conically shaped solid bulbs are connected to the extremities of the bar. The occluder is insertable through an incision in the blood vessel with the arms and bulbs extending in opposite directions along the vessel. A section of the blood vessel is thus sealed off at both ends for anastomosis for other purposes.

7 Claims, 5 Drawing Figures

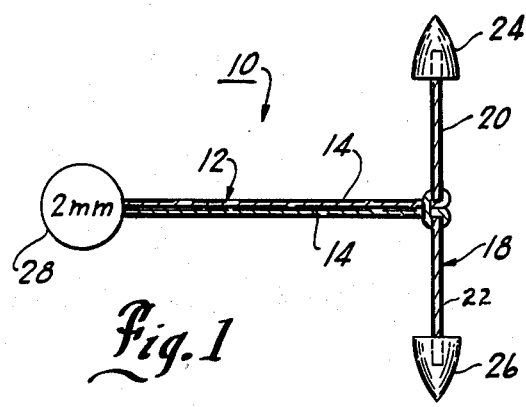
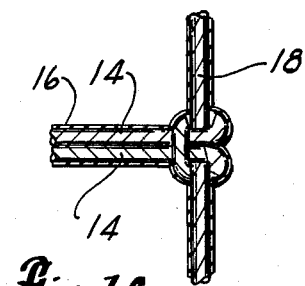
Fig. 1
Fig. 1A
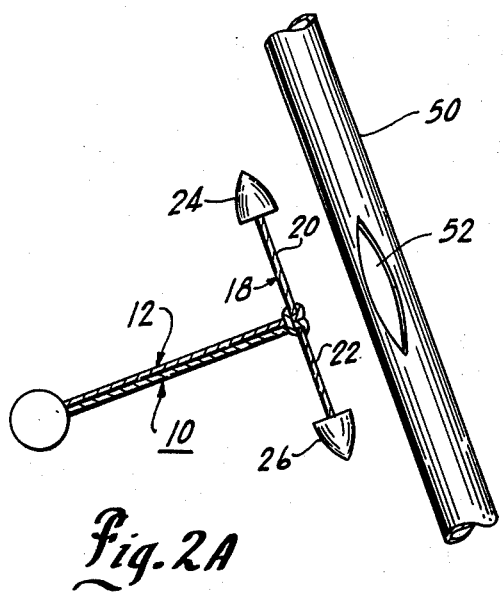
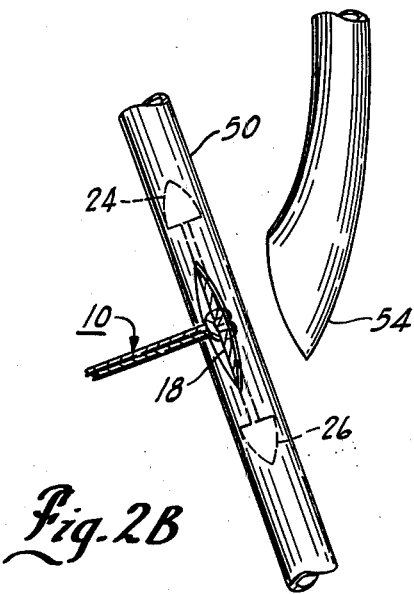
Fig. 2A
Fig. 2B
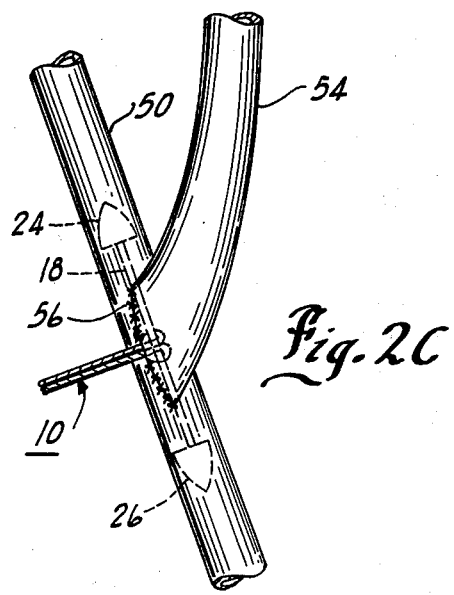
Fig. 2C

BLOOD VESSEL OCCLUSION MEANS SUITABLE FOR USE IN ANASTOMOSIS

BACKGROUND OF THE INVENTION

1. Field of the Invention

The present invention relates to an occluder for sealing off a section of a blood vessel.

2. Description of the Prior Art

In surgical procedures, it is often necessary to seal off a small section of a blood vessel. This need may arise in vascular surgery, including coronary artery by-pass operations in which a blocked portion of the artery is by-passed with another blood vessel so as to restore and insure adequate blood supply to the heart muscle.

In such an operation, a short segment of vein, usually taken from the patient's leg, is used. One end of this blood vessel is connected to the aorta, the major body artery supplying all parts of the body except the lungs. The other end of the vein is connected to the blocked coronary artery below the blockage. The term "anastomosis" refers to the formation of such a passage and by reason of the anastomotic connection between the aorta and the artery, a by-pass around the blockage is provided.

The standard operative technique for a coronary artery by-pass requires clamping off the aorta to terminate blood flow to all the coronary arteries. By-pass connection or grafting then proceeds. The grafting procedure often involves as many as three by-pass grafts and sometimes as many as four or five. It may thus become necessary to clamp off the aorta for an extended period of time. During this time, there is no blood supply to the muscular tissue, or myocardium, of the heart. This prolonged cessation of blood supply can only be deleterious to an already diseased heart. Such clamping off of the aorta may be responsible for the life threatening infarcts which occur in two to five percent of by-pass patients.

SUMMARY OF THE PRESENT INVENTION

The present invention seeks to facilitate vascular surgery by an improved means for sealing off a section of blood vessel during grafting or other operative procedures. In coronary artery by-pass surgical operations, the invention makes it possible to graft the by-pass on the coronary artery without clamping off the aorta, thereby improving the procedure and minimizing trauma to the heart and vascular system. The aorta need be clamped off only for the time during which the by-passing blood vessel is grafted to the aorta.

The occlusion means of the present invention includes a stem having a pair of opposing arms at one end forming a cross bar. An identifying tab may be connected to the other end of the stem. A generally conical or bullet-shaped solid bulb is connected to the extremity of each of the arms. The occlusion means may be formed of silicone rubber or other physiologically inert material.

In use, the arms are inserted in the coronary artery through the incision made at the location where the by-passing graft will occur. The arms and bulbs extend in opposite directions along the blood vessel from the incision to seal off the section of the blood vessel containing the incision. The graft is then made and as the grafting operation nears completion, the occluder is removed just prior to final suturing of the graft.

During this grafting, the stoppage of the blood supply to the heart muscle is confined to the small area where the by-pass is being made and only for the time required for the vein graft, a period of usually less than fifteen minutes.

The use of solid bulbs, in the present invention, provides several advantages over prior art devices. The prior art typically used inflatable cuffs to seal the ends of the arterial section. However, unless extreme care was exercised in fabrication and use, the distention of the cuff by inflation could cause excessive pressure on, and damage to, the interior of the artery. This has led to the use of inflatable cuffs in which the cuff is filled with a sponge-like material which is contracted, for insertion, by drawing a vacuum on the cuff. The vacuum is then released to allow the cuff to expand. The amount of expansion of the cuff could be closely controlled by the amount of sponge-like material in the cuff.

However, such devices tend to prolong the surgery by the time needed for their inflation and deflation. There is always the danger that inadvertent puncture by a scalpel or suturing needle might alter the condition of the cuff to the detriment of the surgery. The structure necessary for inflation tends to increase the size and complexity of the device and interfere with the surgery.

With the present invention, the hardness of the solid bulbs is selected so that the material is soft enough not to cause undue trauma to the artery during use while at the same time being hard enough to establish a seal with the arterial wall. These properties are coupled with those of the cross bar which is sufficiently stiff to prevent the pressure of the blood in the vessel from dislodging bulbs while at the same time being flexible enough to facilitate the insertion and removal of the occlusion means.

BRIEF DESCRIPTION OF THE DRAWING

FIG. 1 is a perspective view of a blood vessel occlusion means of the present invention.

FIG. 1A is a partial view of the stem of the occlusion means shown the manner in which the bar is attached.

FIGS. 2A through 2C are perspective views showing use of the occlusion means in a surgical procedure.

The showings of the Figures are enlarged to facilitate the disclosure of the invention.

DETAILED DESCRIPTION OF THE PREFERRED EMBODIMENT

Turning now to the Figures, there is shown therein an occlusion means 10 of the present invention. Occluder 10 includes elongated stem 12. Stem 12 is preferably formed of a pair of strands 14 of thread. The strands 14 join bar 18 having arms 20 and 22 which provide a generally T-shaped configuration to occluder 10. It will be appreciated that because of the softness and flexibility of the occluder, the device may often assume other configurations. The use of threads 14 to form stem 12 and arms 20 and 22 reduces the diameter of these elements to a minimum to avoid interference with suturing while at the same time providing high tensile strength to the elements.

In a preferred embodiment of the present invention, bar 18 may be formed of a braided polyester thread identified as a #2 suture. The braided construction serves to stiffen the bar as well as faciitating the coating with a material 16, hereinafter described, by allowing impregnation of the thread. The strands forming stem 12 may comprise 0.007" diameter polyester thread.

Stem 12 may be joined to bar 18 by a knot termed a "cats paw", as shown in FIG. 1A. A thread is folded in the center to form parallel strands 14. The folded bight is then rolled around bar 18 and the ends of strands 14 inserted in the loop of the bight, to form the knot, as shown in FIG. 1A.

Bulbs 24 and 26 are connected to the extremities of arms 20 and 22, respectively. While many configurations may be employed, bulbs 24 and 26 are preferably of the rounded cone configuration which typically characterizes a bullet. The shape may be more precisely defined as that formed by the revolution of a lancet arch about a medial axis. A sharp point facilitates entry and movement into the blood vessel. A flat base to the bulb assists in forming a sharp angle with the side of the bulb which resists movement along the blood vessel in a direction of withdrawal.

Bulbs 24 and 26 may be formed by molding. Holes are provided in the bases of the bulbs in which arms 20 and 22 are inserted and retained with an appropriate cement. Occluder 10 may be coated, after assembly, with a smooth, soft, flexible, physiologically inert material 16, such as silicone rubber, as shown in FIG. 1A.

Bulbs 24 and 26 may be formed of a physiologically inert material, such as medical grade silicone rubber. The hardness of the rubber may be controlled by the type and amount of catalyst used to cure the elastomer and the amount of heat and time employed during the curing or vulcanizing process. To achieve the advantages of the present invention, it is necessary to provide a sufficient softness to bulbs 24 and 26 so as not to cause undue trauma when occluder 10 is inserted in a blood vessel yet a sufficient hardness to obtain an adequate seal with the interior of the blood vessel.

Hardness is typically measured by a durometer, such as a Shore A durometer which ascertains the penetration of a specified indentor into a specimen under specified conditions. A shore A hardness in the range of 35 to 60 has been found suitable for bulbs 24 and 26.

Bulbs 24 and 26, so formed have been found to possess the advantage of being hard enough to facilitate and permit entry and movement along the blood vessel and sealing with the walls of the blood vessel, yet being soft enough not to dislodge any sclerotic plaque, during such entry and movement, which may be present in the blood vessel. Such plaque is formed as a calcified deposit in the blood vessel and, if dislodged, may form an embolus in the cardiovascular system.

It is similarly necessary to closely select the properties of bar 18 which separates bulbs 24 and 26 so that the bar is stiff enough to prevent the pressure of the blood from pushing the bulbs towards each other while at the same time is flexible enough to facilitate use of the occluder.

While the exact property of bar 18 to be controlled is its ability to resist axial compressive loading, a more readily available and measurable property is its "stiffness" or flexural modulus: The following test has been devised to measure and compare the stiffness of bar 18. Force is applied to the ends of an initially straight bar until the bar is bent, in a U-shaped configuration, to one half its length. The amount of this force is then measured. A stiffness of bar 18 requiring approximately 3 to 5 grams of force to obtain the above deflection has been found to achieve the results of the invention.

The stiffness of bar 18 is controlled both by the type of material employed, such as the suture material noted above, and the material type and thickness of coating 16.

Bulbs 24 and 26 are dimensioned in accordance with the size of the blood vessel which they must occlude. A series of occluders having bulbs of differing diameters may therefore be provided. For example, the diameter of bulbs 24 and 26 may increase from 1 millimeter to 3 millimeters in 0.25 to 0.5 millimeter increments. The distance between the major diameter of bulbs 24 and 26 when occluder 10 is oriented in a T-shape, as shown in FIG. 1, typically ranges from 15 to 25 millimeters. The length of stem 12 may be 40 to 60 millimeters. Disc 28 may be mounted on the other end of stem 12. Disc 28 serves as a convenient means for grasping occluder 10 and as an indication of its presence. The diameter of bulbs 24 and 26 may be noted on disc 28.

In use, the section of blood vessel 50, such as a coronary artery, to be anastomotized is located and a longitudinal incision 52 made. Occluder 10, in a sterile condition, is quickly inserted in blood vessel 50 through incision 52. The size of occluder 10 is selected to be slightly greater than the inner diameter of blood vessel 50. Arms 20 and 22 and bulbs 24 and 26 are extended along blood vessel 50 in opposite directions from stem 12 located in incision 52, as shown in FIG. 2B. The occluder is usually inserted with little difficulty or loss of blood.

Blood vessel 54, such as a by-passing leg vein graft, to be connected to blood vessel 50 is placed over incision 52. Blood vessel 54 is sutured to blood vessel 50 about incision 52. It has been found that the distortion of blood vessel 50 from the enlargement by bulbs 24 and 26 flares the lips of incision 52, facilitating the suturing. Sutures 56 are prepared about the opening through which stem 12 extends but are not drawn tight. Occluder 10 is then pulled out of artery 50 by grasping disc 28. The suturing of blood vessel 54 to blood vessel 50 is quickly completed to minimize any blood loss.

Various modes of carrying out the invention are contemplated as being within the scope of the following claims particularly pointing out and distinctly claiming the subject matter which is regarded as the invention.

We claim:

1. An occluder adapted to be inserted and removed through an incision in a blood vessel to temporarily seal off a section of said blood vessel which includes the incision, said occluder including:

means for assisting the placement of the occluder in the blood vessel, said means comprising a relatively rigid, elongated stem having a pair of ends;

a pair of flexible arms forming a bar having a central portion thereof connected at one end of said stem, said arms having a diameter smaller than the normal diameter of the blood vessel to be occluded; and a pair of non-inflatable, generally conical bulbs, each of said bulbs being connected at its base to a respective end of said bar, said bulbs having a diameter which is larger than that of the arms and the blood vessel and sufficient hardness to form fluid tight seals with the wall of the blood vessel without dislodging any sclerotic plaque which may be present in the blood vessel, the conical portions of said bulbs being imperforate surfaces to prevent any fluid passage therethrough.

2. The occluder of claim 1 in which the bulbs have a Shore A durometer hardness of about 35 to about 60.

3. The occluder of claim 1 in which the stem and bar provide a generally T-shaped configuration to said occluder and space said bulbs in a direction generally normal to said stem.

4. The occluder according to claim 1 wherein the bulbs are formed of a physiologically inert material.

5. The occluder according to claim 1 wherein the bulbs are formed of silicone rubber.

6. The occluder according to claim 1 wherein the other end of the stem provides a tab suitable for grasping.

7. The occluder of claim 1 wherein the bar is of sufficient stiffness to resist the displacement of said bulbs by fluid pressure in the blood vessel once the occluder is in position.

* * * * *